United States Patent [19]

Bazer et al.

[11] Patent Number: 5,258,367
[45] Date of Patent: Nov. 2, 1993

[54] UTEROFERRIN AND ROSE PROTEINS FOR STIMULATING HEMATOPOIETIC CELLS

[75] Inventors: Fuller W. Bazer; Samuel Gross, both of Gainesville, Fla.

[73] Assignee: University of Florida, Gainesville, Fla.

[21] Appl. No.: 547,025

[22] Filed: Jun. 29, 1990

[51] Int. Cl.[5] .................... A61K 37/02; C07K 15/06; C07K 15/14
[52] U.S. Cl. ........................ 514/6; 530/395; 530/397; 530/400
[58] Field of Search .............. 514/6; 530/395, 397, 530/400

[56] References Cited

U.S. PATENT DOCUMENTS 4,722,998  2/1988  Cantor et al. .................. 530/350
4,810,643  3/1989  Souza ........................... 435/320.1

OTHER PUBLICATIONS

Gross et al., "Uteroferrins are Hematopoietic Growth Factors", 81st Annual Meeting of Am. Assoc. for Cancer Res., Washington, D.C., USA, May 23-26, 1990, Proc. Am. Assoc. Cancer Res. 31(0) 1990, p. 43.
Worthington-White et al., "Uteroferrin and Rose Proteins From Pig Endometrium are Hematopoietic Growth Factors", 22nd Annual Meeting of Soc. for the Study of Reprod. Columbia, Mo., USA, Aug. 6-9, 1989, Biol. Reprod. 40 (Suppl. 1), 1989, p. 112.
Baumbach et al., "Uteroferrin has N-Asparagine-Linked High-Mannose-Type Digosaccharides . . . ", *PNAS* USA vol. 81, May 1984, pp. 2985-2989.
Guilbert et al., "Partial Replacement of Serum by Selenite, Transferrin, Albumin . . . ", *Nature*, vol. 263, Oct. 14, 1976, pp. 594-595.

Primary Examiner—Jeffrey E. Russel
Attorney, Agent, or Firm—J. R. Wetherell, Jr.

[57] ABSTRACT

Method of using uteroferrin and rose for stimulating proliferation of hematopoietic cells.

17 Claims, 7 Drawing Sheets

UTEROFERRIN AND ROSE PROTEINS FOR STIMULATING HEMATOPOIETIC CELLS

FIELD OF THE INVENTION

This invention relates to uteroferrin and rose proteins and their use to stimulate hematopoietic cells.

DESCRIPTION OF THE BACKGROUND ART

Uteroferrin is a purple colored, progesterone-induced glycoprotein containing two molecules of iron which is secreted by uterine endometrial epithelium of pigs (F. W. Bazer and R. M. Roberts, *J. Exp. Zool.*, 228:373, 1983; R. M. Roberts and F. W. Bazer, *Bio Essays*, 1:8, 1984). Uteroferrin exists as a 35,000 Mr polypeptide having a purple color and as a heterodimer (Mr=80,000) with one of three "uteroferrin-associated proteins" which have high amino acid sequence homology with serine protease inhibitors (M. K. Murray, et al., *J. Biol. Chem.*, 264:4143, 1989). The heterodimer has a rose color, but the biochemical and biological significance of the rose-form of uteroferrin and the uteroferrin-associated proteins is not known. Uteroferrin carries high mannose carbohydrate with the mannose-6-$PO_4$ recognition marker for lysosomal enzymes (G. A. Baumbach, et al., *Proc. Nat. Acad. Sci.*, U.S.A., 81:2985, 1984) and has acid phosphatase activity (D. C. Schlosnagle, et al, *J. Biol. Chem.* 249:7574, 1974). During pregnancy, uteroferrin is transported from uterine secretions into the fetal-placental circulation by specialized placental structures called areolae (R. H. Renegar, et al., *Biol. Reprod.*, 27:1247, 1982). The mannose residues on uteroferrin are responsible for uteroferrin being targeted to reticuloendothelial cells of the fetal liver, the major site of hematopoiesis in fetal pigs (P. T. K. Saunders, et al., *J. Biol. Chem.*, 260:3658, 1985).

Administration of radiolabelled iron to pigs results in endometrial secretion of uteroferrin carrying radiolabelled iron and incorporation of radiolabelled iron into fetal erythrocytes and cells of liver, spleen and bene marrow (C. A. Ducsay, et al., *Biol. Reprod.*, 26:729, 1982; C. A. Ducsay, et al., *J. Anim. Sci.*, 59:1303, 1984). Uteroferrin gives up its iron to fetal transferrin in allantoic fluid with a half-life of 12 to 24 hours (W. C. Buhi, et al, *J. Biol. Chem.*, 257:1712, 1982). Further, administration of iron dextran to pregnant pigs on days 50, 60 and 70 (term is at 115 days), the period of maximum secretion of uteroferrin by the endometrium, results in a 20% increase in iron stores in neonatal piglets (C. A. Ducsay, et al., *Biol. Reprod.*, 26:729, 1982; C. A. Ducsay, et al., *J. Anim. Sci.*, 59:1303, 1984). These results suggest a role for uteroferrin in transplacental transport of iron. However, after Day 75 of gestation, translation of mRNA for uteroferrin decreases rapidly (R. C. M. Simmen, et al., *Mol. Endocrinol.* 2:253, 1988), secretion of uteroferrin by endometrial explant cultures declines (S. M. M. Basha, et al., *Biol. Reprod.*, 20:431, 1979), and the amount of uteroferrin in allantoic fluid decreases dramatically (F. W. Bazer, et al., *J. Anim. Sci.*, 41:1112, 1975). This suggests that an alternate mechanism for transplacental iron transport becomes operative between Days 75 and term when fetal/placental demands for iron are increasing (C. A. Ducsay, et al., *Biol. Reprod.*, 26:729, 1982; C. A. Ducsay, et al., *J. Anim. Sci.*, 59:1303, 1984).

Uteroferrin from pig uterus is a tartrate-resistant acid phosphatase with many properties in common with the Type 5 acid phosphatase in human placenta (C. M. Ketcham, et al., *J. Biol. Chem.*, 260:5768, 1986), chondrocytes of humans with osteoclastic bone tumors and spleens of humans with hairy cell leukemia, Gaucher's disease and Hodgkin's disease. In addition, uteroferrin has characteristics similar to those for purple acid phosphatases from bovine, rat, mouse, and pig spleen, as well as bovine milk, bovine uterine secretions, equine uterine secretions, and rat bone (C. M. Ketcham, et al., *J. Biol. Chem.* 260:5768, 1985).

In the medical community there has long been a recognition of various disorders involving the hematopoietic system. These disorders include the anemias; myeloproliferative diseases; primary bone marrow dysfunctions, especially those involving pancytopenia; and the leukemias.

Depending on the nature of the hematopoietic disorder, various therapies may be used. Unfortunately, for many of these disorders, no adequate therapeutic approach is available and treatment consists primarily of basic management of the patient. Alternatively, where therapeutic agents are available, there are often significant toxic side effects associated with their use.

In order to circumvent the toxic side effects often associated with traditional chemotherapy, in recent years considerable research has focused on the discovery and use of "natural" hematopoietic growth factors, such as erythropoietin, or bone marrow transplants, as alternative forms of therapy. Although these modalities appear promising, they also have their limitations. For example, the use of bone marrow transplants has been severely limited due to the extreme difficulty in obtaining bone marrow which is histocompatible with the recipient. As a result, there continues to be considerable need for other agents capable of stimulating cells of the hematopoietic system.

SUMMARY OF THE INVENTION

The present invention arose out of the discovery that uteroferrin and rose could be used as hematopoietic growth factors to stimulate hematopoietic cells. This stimulation appears to act at a more primitive level of stem cell development than has previously been observed with other hematopoietic growth factors. Thus, the present invention relates to the therapeutic use of uteroferrin and rose as hematopoietic growth factors.

Various other aspects and attendant advantages of the present invention will be more fully appreciated from an understanding of the following detailed description in combination with the accompanying example.

DETAILED DESCRIPTION OF THE INVENTION

Uteroferrin and rose may be obtained by a variety of different methods. These substances may be obtained from uterine flushings of pigs (Baumbach, et al., *Proc. Natl. Acad. Sci.*, U.S.A., 81:2985, 1984) or allantoic fluid (Baumbach, et al., *J. Biol. Chem.*, 261:12869, 1986). Human uteroferrin, also referred to as human placental Type V acid phosphatase, can be purified as described by C. M. Ketcham, et al., (*J. Biol. Chem.*, 260:5768, 1986). Uteroferrin has also been produced by recombinant techniques (Simmen, et al., *Molecular Endocrinology*, 2:253, 1988; C. M. Ketcham, et al., *J. Biol. Chem.*, 264:557, 1989).

The term "hematopoietic growth factor" is intended to include uteroferrin and multichain variants of uteroferrin, such as rose, and their functional derivatives. The term "functional derivatives" pertains to polypeptides that may contain or lack one or more amino acids that may not be present in uteroferrin or rose, wherein these polypeptides are functionally similar to uteroferrin or rose. Such polypeptides are termed "functional derivatives", if they demonstrate hematopoietic activity which is substantially similar to uteroferrin or rose.

The term "therapeutically effective" means that the amount of hematopoietic growth factor used is of sufficient quantity to stimulate the proliferation of hematopoietic cells. The dosage ranges for the administration of the hematopoietic growth factor of the invention are those large enough to produce the desired effect in which the hematopoietic cells show some degree of stimulation. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications. Dosage can vary from about 10 $\mu$g/kg/dose to about 500 $\mu$g/kg/dose, preferably about 20 $\mu$g/kg/dose to about 200 $\mu$g/kg/dose, most preferably from about 50 to about 100 $\mu$g/kg/dose in one or more dose administrations daily, for one or several days.

Studies indicate that the hematopoietic growth factor uteroferrin is phenotypically conserved. Thus, according to the method of the invention, uteroferrin from a first species can be used in a second species to stimulate the hematopoietic cells of the second species, although the activity of uteroferrin of a given species is usually optimal when used to treat a member of that same species.

The hematopoietic growth factor of the invention can be administered parenterally or by gradual perfusion over time. The hematopoietic growth factor of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In order to form a pharmaceutically acceptable composition suitable for effective administration, such compositions will contain an effective amount of the hematopoietic growth factor, or its functional derivatives, together with a suitable amount of a carrier vehicle.

Additional pharmaceutical methods may be employed to control the duration of action. Controlled release preparations may be achieved by the use of polymers to complex or adsorb the hematopoietic growth factor or its functional derivatives. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the hematopoietic growth factor into particles of a polymeric material such as polyesters, polyamino acids, hydrogels, poly (lactic acid) or ethylene vinylacetate copolymers. Alternatively, instead of incorporating the hematopoietic growth factor into these polymeric particles, it is possible to entrap the hematopoietic growth factor in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (16th Ed., A. Oslo, ed., Mack, Easton, Penn., 1980).

The method of the invention can also be used ex vivo to stimulate hematopoietic cell proliferation. For example, where a patient is receiving an allogeneic bone marrow graft from a donor, the donor cells can be treated with the hematopoietic growth factors of the invention and, if desired, co-cultured for a period of time, before infusion into the recipient. Such treatment can also be utilized, for example, where it is desirable for the patient to undergo an autologous marrow graft wherein the patient's marrow is treated chemotherapeutically and/or radiotherapeutically before re-infusion into the same patient. Ex vivo treatment using the hematopoietic growth factors of the invention is particularly relevant, for example, where the abnormal bone marrow must be eliminated and replaced with normal marrow. Other diseases where ex vivo therapy would be useful are acute leukemia, and other hematologic malignancies, where the complete destruction of the leukemic cell population and, unavoidably, normal marrow cells by intensive chemoradiotherapy is required. Techniques for ex vivo treatment of bone marrow cells are well known, or readily discernable, to those of skill in the art without undue experimentation.

The ex vivo method of the invention can also be modified by the addition of an iron source, or compounds of similar biologic activity such as transferrin or $FeCl_3$, to the proliferating cell culture, in combination with uteroferrin or rose. Co-culturing with transferrin appears to enable much lower concentrations of hematopoietic growth factor to be utilized than when the hematopoietic growth factor is administered alone. When transferrin is administered in combination with the hematopoietic growth factor a dosage of transferrin of from about 100 to about 700 $\mu g/ml$, preferably from about 400 to about 600 $\mu g/ml$, most preferably from about 500 to about 600 $\mu g/ml$, is utilized.

The invention also relates to a method for preparing a medicament or pharmaceutical composition comprising the hematopoietic growth factor of the invention, the medicament being used for therapy to stimulate the proliferation of hematopoietic cells.

The above disclosure generally describes the present invention. A more complete understanding can be obtained by reference to the following specific examples which are provided herein for purposes of illustration only, and are not intended to limit the scope of the invention.

EXAMPLE

COMPARATIVE STIMULATORY EFFECT OF UTEROFERRIN AND ROSE ON VARIOUS HEMATOPOIETIC CELL TYPES

Figure 1A:
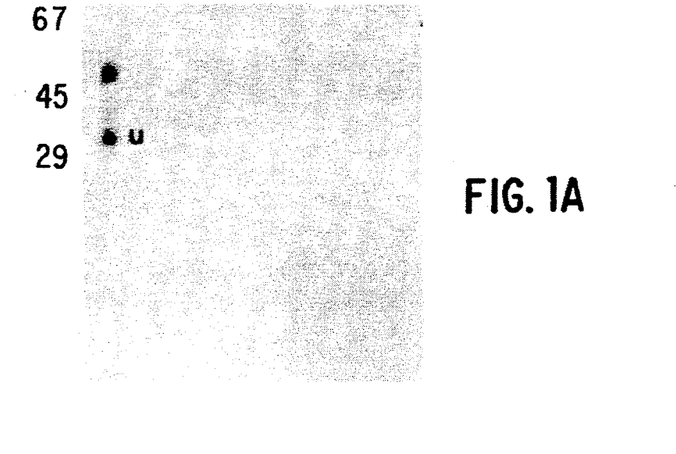
FIG. 1A-C Two-dimensional polyacrylamide gels demonstrating that the rose-colored protein is a heterodimer of uteroferrin (u) and one of three other proteins that are also basic (Panel A); the basic control protein contains a heterogenous population of basic proteins, mostly of larger molecular weight than uteroferrin (Panel B), and highly purified uteroferrin (Panel C).
Figure 1B:
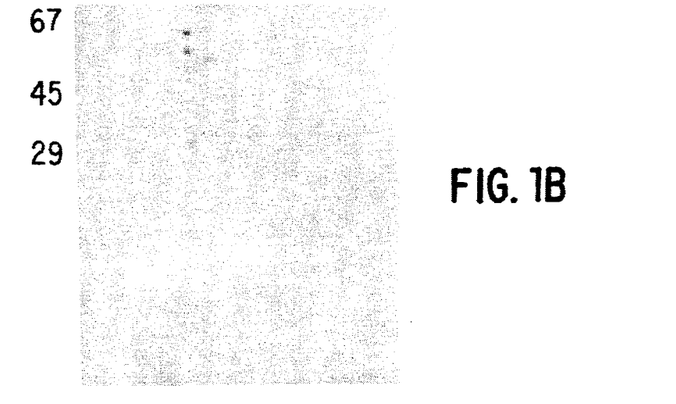
Figure 1C:
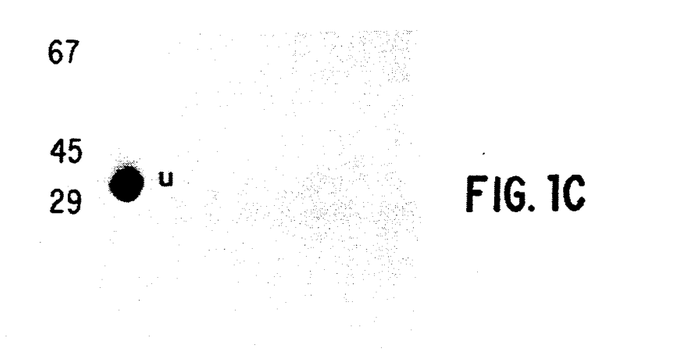

Uteroferrin, the rose-colored heterodimer, and an unidentified basic protein with a molecular weight slightly greater than that of "rose" were individually purified (FIG. 1) from uterine secretions of pseudopregnant pigs (G. M. Baumbach, et al., *J. Biol. Chem.*, 261:12869, 1986) as previously described (Baumbach, et al., *Proc. Nat. Acad. Sci., U.S.A.*, 81:2985, 1984; Murray, et al., *J. Biol. Chem.*, 264:4143, 1989). These purified components were tested for colony stimulating factor (CSF) activity with respect to GM cells (Iscove, et al., *Blood*, 37:1, 1971), E cells (Ogawa, et al., *Blood*, 48:407, 1976) and GEMM cells (Fauser, et al., *Blood*, 53:1023, 1979).

These assays detect colony forming units (CFU) of granulocytes (CFU-GM), erythrocytes (CFU-E), or the mixed lineage primitive granulocyte/macrophage/erythrocyte/megakaryocyte colonies (CFU-GEMM). Light density nonadherent mononuclear cells were isolated from human and pig bone marrow and fetal bone marrow from pigs (Days 65 and 101 of gestation). Additionally, tissue samples were obtained from neonatal piglet liver (Days 65 and 101 of gestation) and embryonic yolk sac cells (Day 21 of gestation). Cells were cultured in Minimal Essential Medium-α (MEMα) with 0.9% methyl cellulose, 20–30% fetal bovine serum and 0.6% I-glutamine for 7 days (CFU-E) and for 14 days (CFU-GM and CFU-GEMM) in a humidified incubator containing 5% $CO_2$ in air. The positive control cultures contained recombinant human GM-CSF (rhGM-CSF, 50 units/ml or 1 ng) to stimulate CFU-GM, recombinant human erythropoietin (rhEPO, 2 units/ml or 20 ng) to stimulate CFU-E or rhGM-CSF+rhEPO to stimulate CFU-GEMM.

Uterine secretions were obtained from a pseudopregnant pig and fractionated into basic and acidic proteins (S. M. M. Basha, et al., *Biol. Reprod.*, 20:431, 1979). The acidic and basic proteins were then fractionated further using Sephadex S-300 gel filtration chromatography. None of the acidic proteins had detectable hematopoietic growth factor activity. Only uteroferrin and "rose", in basic proteins from uterine secretions from pigs, had hematopoietic growth factor. Uteroferrin and rose were purified further (FIG. 1) and tested at $10^{-9}, 10^{-7}, 10^{-5}, 10^{-3}$, and $10^{-1}$ mg/ml for hematopoietic growth factor activity. A basic protein fraction eluting from the Sephadex S-300 gel filtration prior to "rose" was used as the negative control protein(s) in this study since those proteins had been subjected to identical chromatographic procedures as uteroferrin and rose. These negative control proteins are noted as "yellow" herein, due to their yellow coloration.

Figure 2A:
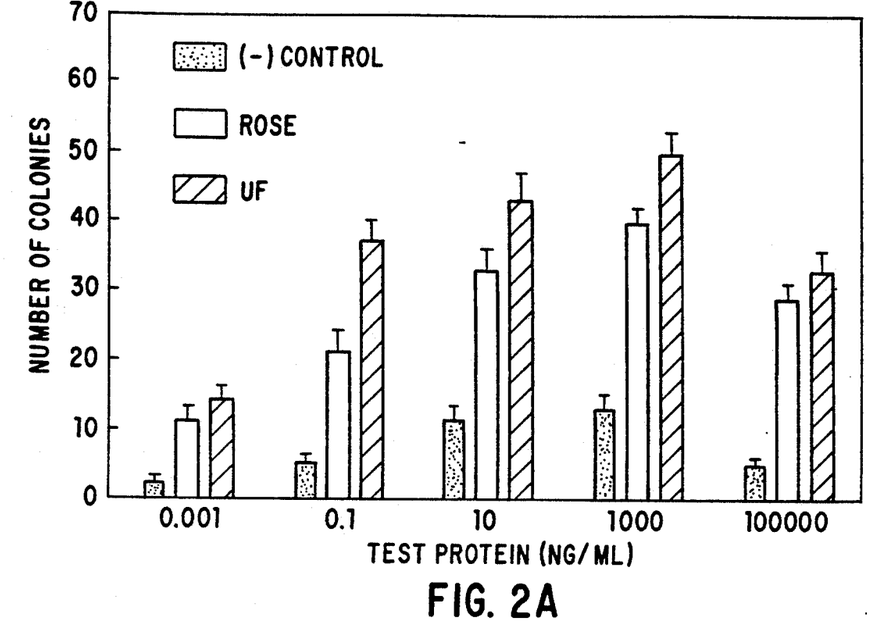
FIG. 2A-C Dose-response effects of uteroferrin, rose and the basic negative control protein(s) on nonadherent human bone marrow cells when assayed for CFU-GM, CFU-E, and CFU-GEMM activities. A colony was defined as a group of 50 or more cells. The GEMM colonies included erythrocytes, granulocytes, monocytes/marcrophages and megakaryocytes. The GM colonies were composed of granulocytes only (67%), macrophages and granulocytes (21%) or macrophages only (12%). The erythroid colonies were composed of erythrocytes. The number of colonies (mean±S. E. M.) that formed in response to rhGM-CSF (1 ng; CFU-GM), rhEPO (80 ng; CFU-E) and rhGM-CSF+rhEPO (CFU-GEMM) were 83±8, 84±7, and 21±3, respectively.
Figure 2B:
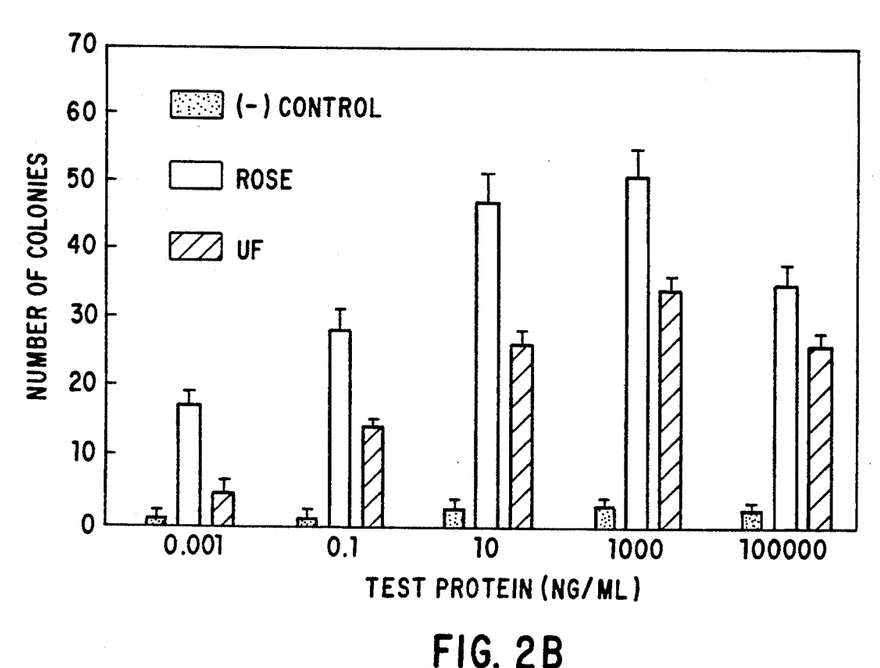
Figure 2C:
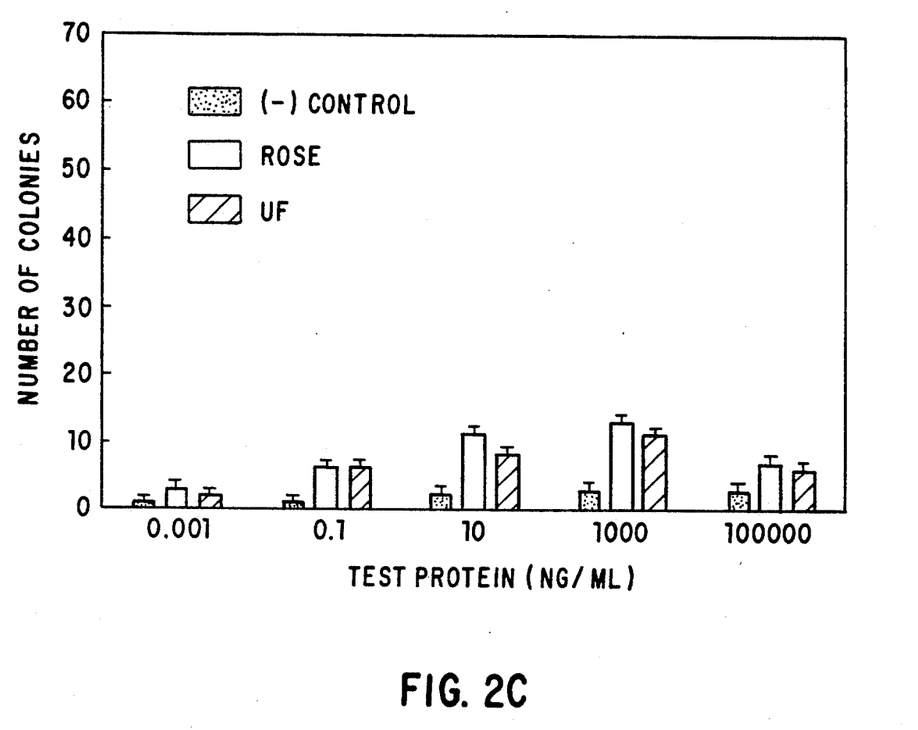
Figure 3A:
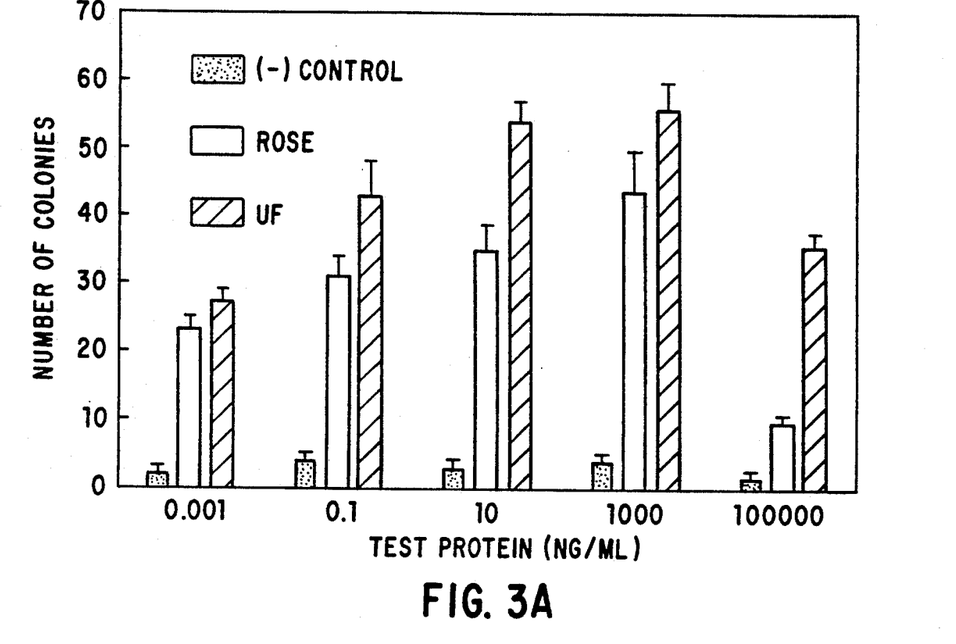
FIG. 3A–C Dose-response effects of uteroferrin, rose and the basic negative control protein on nonadherent neonatal pig bone marrow cells when assayed for CFU-GM, CFU-E, and CFU-GEMM activities. The numbers of colonies (mean±S. E. M.) that formed in response to rhGM-CSF (1 ng; CFU-GM), rhEPO (80 ng; CFU-E), and rhGM-CSF+rhEPO (CFU-GEMM) were 21±3, 19±4, and 7±1, respectively.
Figure 3B:
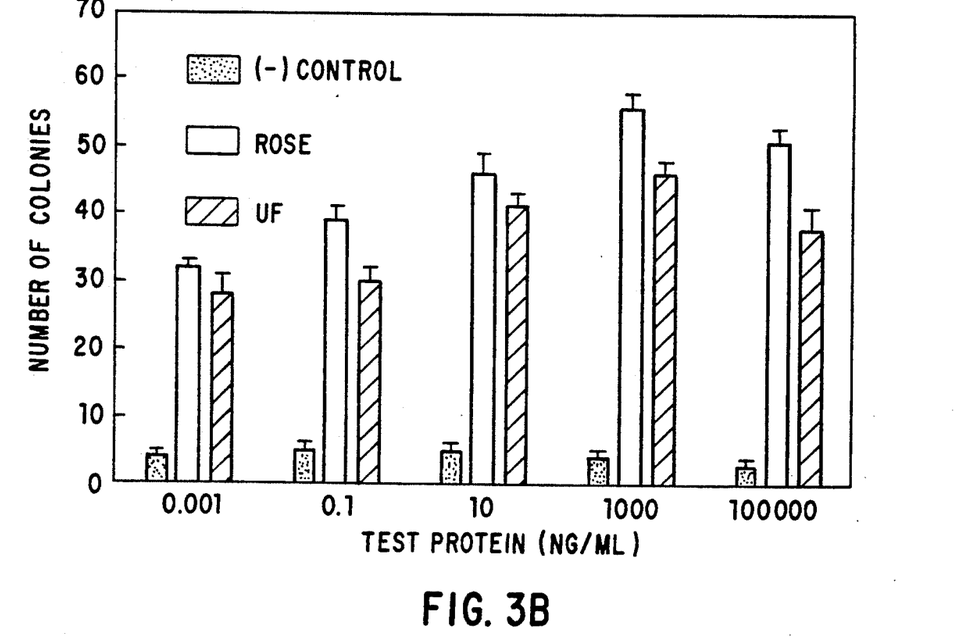
Figure 3C:
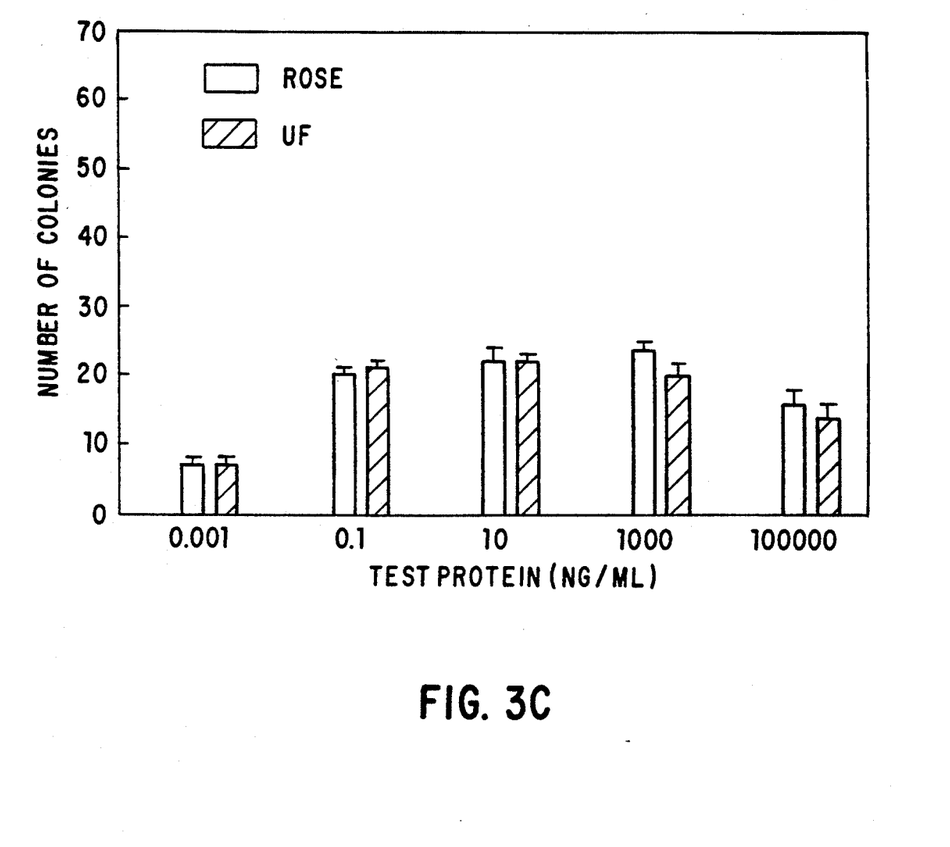
Figure 4A:
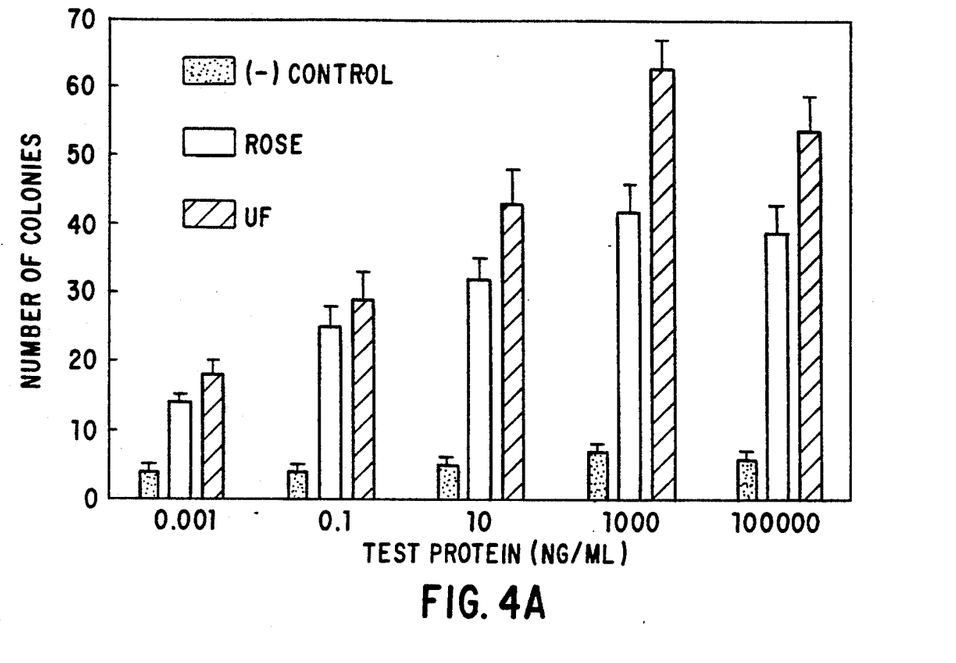
FIG. 4A–C Dose-response effects of uteroferrin, rose and the basic negative control protein on nonadherent neonatal pig liver cells when assayed for CFU-GM, CFU-E, and CFU-GEMM activities. The numbers of colonies (mean±S.E.M.) that formed in response to rhGM-CSF (1 ng; CFU-GM), rhEPO (80 ng; CFU-E), and rhGM-CSF+rhEPO (CFU-GEMM) were 11±3, 6±1, and 3±1, respectively.
Figure 4B:
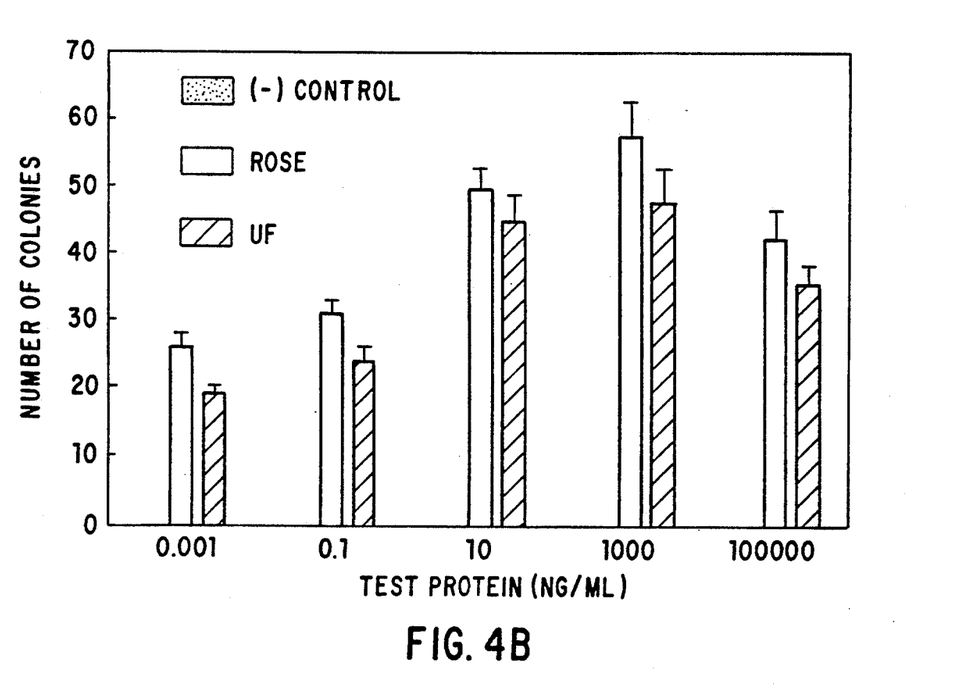
Figure 4C:
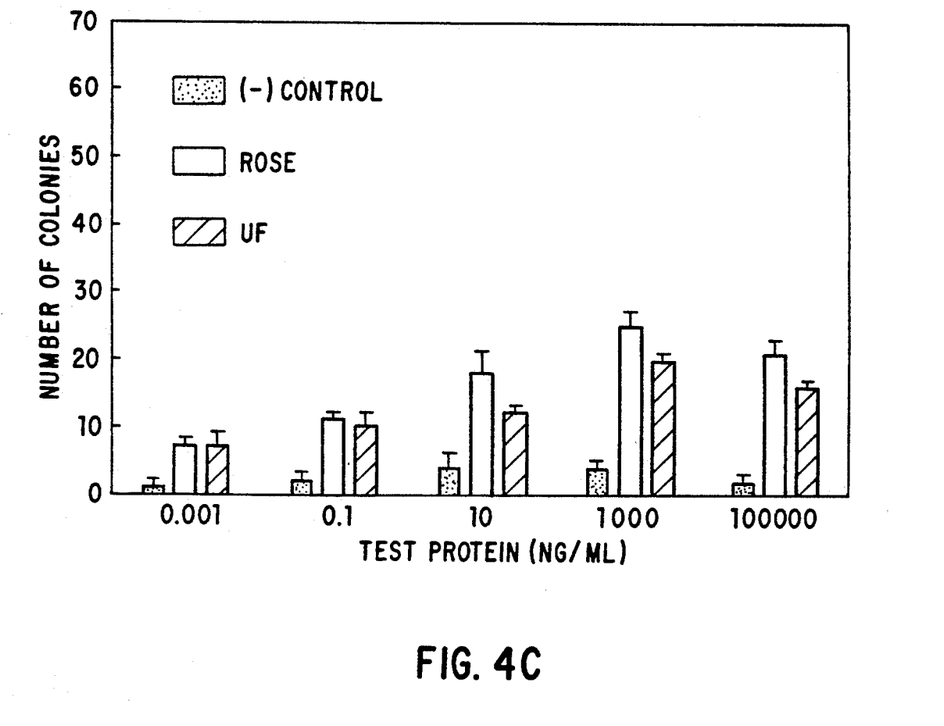

At peak activity ($10^{-3}$ mg/ml) colony forming responses to uteroferrin and rose were greater ($P<0.01$) than for the negative control proteins when added to cultures of hematopoietic stem cells from human bone marrow (FIGS. 2A, B, and C), neonatal piglet bone marrow (FIGS. 3A, B, and C) and neonatal piglet liver (FIGS. 4A, B, and C). Uteroferrin and rose were not as stimulatory to human bone marrow cells as human rhGM-CSF, rhEPO, or rhGM-CSF+rhEPO. However, both uteroferrin and rose were more stimulatory than recombinant human hematopoietic growth factors when nonadherent hematopoietic stem cells were from neonatal piglet bone marrow and liver; a result consistent, since it would be expected that a factor would be optimal when used within the same species from which the factor was derived. In general, uteroferrin has greater CFU-GM activity, while rose has greater CFU-E and CFU-GEMM activity regardless of the source of stem cells. It is especially significant that uteroferrin and rose alone can stimulate CFU-GEMM whereas the positive control cultures required a combination of rhGM-CSF and rhEPO to obtain similar biological activity.

In another study, uteroferrin and rose were found to possess hematopoietic growth factor activity when added to cultures of pig hematopoietic stem cells from fetal spleen, fetal bone marrow, and fetal liver from Days 65 and 101 of gestation (Table 1). In each case, uteroferrin and rose had more potent CFU activities than rhGM-CSF, rhEPO and rhGM-CSF+rhEPO.

TABLE 1

| CELL SOURCE | TREATMENT | DAY 65 | | | DAY 101 | | |
|---|---|---|---|---|---|---|---|
| | | CFU-GM | CFU-E | CUF-GEMM | CFU-GM | CFU-E | CUF-GEMM |
| FETAL PIG SPLEEN | UTEROFERRIN | 32 ± 3 | 22 ± 3 | 17 ± 2 | 26 ± 2 | 10 ± 1 | 10 ± 1 |
| | ROSE PROTEIN | 26 ± 1 | 15 ± 2 | 21 ± 3 | 20 ± 2 | 10 ± 2 | 13 ± 1 |
| | YELLOW PROTEIN | 6 ± 2 | 8 ± 1 | 3 ± 1 | 2 ± 1 | 0 ± 0 | 0 ± 0 |
| | POSITIVE CONTROL | 13[a] | 9[b] | 7[c] | 14 | 9 | 6 |
| | NEGATIVE CONTROL[d] | 0 | 0 | 1 | 0 | 0 | 0 |
| FETAL PIG BONE MARROW | UTEROFERRIN | 28 ± 5 | 22 ± 3 | 11 ± 1 | 29 ± 1 | 21 ± 5 | 14 ± 1 |
| | ROSE PROTEIN | 17 ± 3 | 5 ± 1 | 7 ± 3 | 31 ± 2 | 27 ± 1 | 18 ± 2 |
| | YELLOW PROTEIN | 1 ± 1 | 1 ± 1 | 0 | 1 ± 1 | 1 ± 1 | 1 ± 1 |
| | POSITIVE CONTROL | 9 | 6 | 4 | 16 | 14 | 6 |
| | NEGATIVE CONTROL | 0 | 0 | 0 | 0 | 0 | 0 |
| FETAL PIG LIVER | UTEROFERRIN | 22 ± 3 | 8 ± 2 | 16 ± 1 | 25 ± 2 | 8 ± 1 | 22 ± 2 |
| | ROSE PROTEIN | 15 ± 3 | 8 ± 2 | 16 ± 3 | 29 ± 2 | 10 ± 1 | 15 ± 1 |
| | YELLOW PROTEIN | 0 ± 0 | 3 ± 1 | 1 ± 1 | 1 ± 1 | 0 | 0 |
| | POSITIVE CONTROL | 9 | 5 | 3 | 21 | 5 | 12 |
| | NEGATIVE CONTROL | 0 | 1 | 0 | 0 | 0 | 0 |

[a]positive control for CFU-GM is rhGM-CSF (0.1 mg/ml)
[b]positive control for CFU-E rhEPO (2 ng/ml)
[c]positive control for CFU-GEMM is rhGM-CSF + rhEPO
[d]negative control for CFU-GM CFU-E, and CFU-GEMM is the absence of rhGM-CSF and rhEPO Another study was done to investigate the possible role of uteroferrin as an iron donor in stimulating hematopoietic cell stimulation. Various hematopoietic cell types from various tissues were purified as described above and cultured in the presence of different concentrations of uteroferrin in the absence or presence of a constant amount of transferrin. Here, the effect of hematopoietic growth factor was measured using a method which combines CFU-GEMM and BFU-E (burst forming units) in a single system along with the CFU-GM method (Ash, et al., Blood, 58:309, 1981). The media used in this technique was modified by using Iscove's Modified Dulbecco's Medium with 2ME ($2 \times 10^{-5}$M). Interleukin-3(IL-3) was added (100 U) to the controls and rhEPO was used at a concentration of 1 U(10 ng).

TABLE 2

EFFECT OF TRANSFERRIN AND UTEROFERRIN INTERACTION ON HUMAN HEMATOPOIETIC STEM CELLS

| TREATMENT[a] | DOSE | CFU-GM | BFU-E[b] | CFU-GEMM |
|---|---|---|---|---|
| UTEROFERRIN | $10^{-1}$ | 26 ± 2 | 51 ± 3 | 12 ± 1 |
| | $10^{-3}$ | 49 ± 6 | 142 ± 27 | 23 ± 2 |
| | $10^{-5}$ | 38 ± 9 | 124 ± 22 | 19 ± 2 |
| | $10^{-7}$ | 26 ± 4 | 76 ± 9 | 14 ± 1 |
| | $10^{-9}$ | 20 ± 2 | 41 ± 8 | 6 ± 1 |
| | $10^{-11}$ | 8 ± 1 | 12 ± 2 | 1 ± 1 |
| UTERO-FERRIN + TRANSFERRIN (600 µg/ml) | $10^{-1}$ | 6 ± 1 | 16 ± 1 | 3 ± 1 |
| | $10^{-3}$ | 12 ± 2 | 36 ± 6 | 6 ± 1 |
| | $10^{-5}$ | 18 ± 6 | 87 ± 11 | 7 ± 1 |
| | $10^{-7}$ | 37 ± 4 | 126 ± 24 | 16 ± 3 |
| | $10^{-9}$ | 28 ± 5 | 107 ± 16 | 11 ± 2 |
| | $10^{-11}$ | 6 ± 1 | 43 ± 7 | 4 ± 1 |

[a]None of the cell types showed colony growth when tested with transferrin alone (600 µg/ml).
[b]burst forming units As shown in Table 2, the presence of transferrin enabled comparable levels of cell stimulation to be achieved at significantly lower levels of uteroferrin.

Results of this study are the first to indicate that progesterone-induced uterine secretory proteins, uteroferrin and rose, effect differentiation of primitive nonadherent hematopoietic stem cells and that the effect is not species specific.

In order to investigate the stimulatory effect of uteroferrin from other species, human uteroferrin was purified and tested with various human hematopoietic cell types (Table 3). In this study, positive and negative controls were as previously described.

TABLE 3

EFFECT OF HUMAN UTEROFERRIN ON VARIOUS HUMAN BONE MARROW CELLS

| TREATMENT | CFU-GM | BFU-E | CFU-GEMM |
|---|---|---|---|
| UTEROFERRIN | 42 | 127 | 22 |
| POSITIVE CONTROL | 88 | 197 | 35 |
| NEGATIVE CONTROL | 2 | 0 | 0 |

These results show that uteroferrin is capable of inducing significant proliferation of the bone marrow cells tested and, unlike the positive control, could act alone to stimulate GEMM cells.

The invention now being fully described, it will be apparent to one of ordinary skill in the art that many changes and modifications can be made without departing from the spirit or scope of the invention.

We claim:

1. A method of stimulating hematopoietic cells in an animal with a hematopoietic disorder comprising administering to the animal a therapeutically effective amount of a hematopoietic stem cell growth factor, wherein the growth factor is selected from the group consisting of uteroferrin and rose, and functional derivatives thereof capable of acting alone to stimulate GEMM cells.

2. The method of claim 1, wherein the administration is in vivo.

3. The method of claim 2, wherein the administration is parenteral.

4. The method of claim 3, wherein the parenteral administration is by subcutaneous, intramuscular, intraperitoneal, intracavity, transdermal, or intravenous injection.

5. The method of claim 1, wherein the hematopoietic cells are from a first species and the hematopoietic growth factor is from a second species.

6. The method of claim 1, wherein the animal is human.

7. The method of claim 1, wherein the hematopoietic growth factor is human derived.

8. The method of claim 1, wherein the hematopoietic growth factor is pig derived.

9. The method of claim 1, wherein the hematopoietic cells are stimulated ex vivo.

10. The method of claim 9, wherein the hematopoietic growth factor is used in combination with an iron source.

11. The method of claim 10, wherein the iron source is selected from the group consisting of transferrin and FeCl$_3$.

12. The method of claim 1, wherein the administration is at a dosage of about 10 μg/kg/dose to about 300 μg/kg/dose.

13. The method of claim 1, wherein the administration is at a dosage from about 20 μg/kg/dose to about 200 μg/kg/dose.

14. The method of claim 1, wherein the administration is from about 50 μg/kg/dose to about 100 μg/kg/dose.

15. The method of claim 11, wherein the transferrin is used at a concentration of about 100 μg/ml to about 700 μg/ml.

16. The method of claim 11, wherein the transferrin is used at a concentration from about 400 μg/ml to about 600 μg/ml.

17. The method of claim 11, wherein the transferrin is used at a concentration from about 500 μg/ml to about 600 μg/ml.

* * * * *